(12) United States Patent
Lloyd

(10) Patent No.: US 7,233,346 B1
(45) Date of Patent: Jun. 19, 2007

(54) DIFFERENTIAL IMAGING METHOD AND SYSTEM

(75) Inventor: Jack Lloyd, Panama City, FL (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 827 days.

(21) Appl. No.: 10/706,476

(22) Filed: Nov. 10, 2003

Related U.S. Application Data

(63) Continuation of application No. 09/119,078, filed on Jul. 14, 1998, now abandoned.

(51) Int. Cl.
*H04N 7/00* (2006.01)
*H04N 5/217* (2006.01)

(52) U.S. Cl. .................. 348/31; 348/81; 348/122; 348/241

(58) Field of Classification Search .......... 348/31, 348/81, 122, 241
See application file for complete search history.

(56) References Cited

U.S. PATENT DOCUMENTS

| | | | | | |
|---|---|---|---|---|---|
| 5,034,810 | A | * | 7/1991 | Keeler | 348/31 |
| 5,047,783 | A | * | 9/1991 | Hugenin | 342/179 |
| 5,233,415 | A | * | 8/1993 | French et al. | 348/31 |
| 5,303,051 | A | * | 4/1994 | Levesque et al. | 348/31 |
| 5,506,616 | A | * | 4/1996 | Scheps | 348/31 |
| 5,929,443 | A | * | 7/1999 | Alfano et al. | 250/341.3 |
| 6,008,486 | A | * | 12/1999 | Stam et al. | 250/208.1 |
| 6,032,070 | A | * | 2/2000 | Flock et al. | 600/473 |
| 6,963,354 | B1 | * | 11/2005 | Scheps | 348/31 |

* cited by examiner

*Primary Examiner*—Lin Ye
(74) *Attorney, Agent, or Firm*—James T. Shepherd

(57) ABSTRACT

A differential imaging system is particularly efficacious for detecting objects in high dispersion or light-scattering mediums, such as seawater. Such a device especially useful in mine detection. A single burst of illumination is used as the light sensitive portion of the system is gated so as to collect at least two images of reflected light from the same burst of illumination. The first image is modified and subtracted from the second image to remove the common noise, and to further enhance the image of the object to be detected.

17 Claims, 2 Drawing Sheets

DIFFERENTIAL IMAGING METHOD AND SYSTEM

This is a continuation application of co-pending application Ser. No. 09/119,078 filed Jul. 14, 1998 now abandoned.

TECHNICAL FIELD

The present invention relates generally to the detection of objects in a high dispersion medium such as saltwater. In particular, the present invention is directed to a differential imaging system which is capable of canceling out much of the light-scattering interference caused by saltwater in order to more sharply provide an image of a scanned scene and an object in that scene.

BACKGROUND ART

When light propagates through a uniform, homogeneous medium, it travels in straight lines. However, when inhomogeneities are introduced into the propagation medium, light is scattered by these inhomogeneities, with some scattering occurring in all directions. Light scattered from inhomogeneities in the medium which reach the receiver are a noise source, as this light does not contain information about a scene (including a specified object) which the observer desires to view. As such, it represents a signal which tends to lower the available scene contrast from what it would be without the scattering. The scattering is a function of the type, size (size distribution), material, and spatial distribution of the scattering inhomogeneities. In a water medium such as saltwater, this spatial distribution can change on a rapid ($\mu$s) basis.

Previous approaches to achieving differential imaging fall into two broad categories:

(1) using a single camera, with two successive light pulses being used to obtain the two signal returns; and, (2) using two cameras with gates temporally offset. Both approaches have substantial drawbacks, as indicated below.

Using a single camera imaging successive light pulses at different gate delays relies on the spatial stability of the medium. In most cases, a relatively low repetition rate laser is used as the illumination source. One example of this type of a system is disclosed in U.S. Pat. No. 5,631,704 to Dickinson et al., issued May 20, 1997, and incorporated herein by reference.

Typically, a 30 Hz laser is used, giving a time delay between return (1) and return (2) on the order of 33 ms. In such an arrangement, the exact distribution of scatterers in the medium has changed significantly during the subject time frame, thereby resulting in a scattering pattern which is no longer identical. Even if the magnitudes of the scatterings are similar, the detailed patterns are usually different. Such a scheme may be acceptable provided the camera is effectively stationary over the time between gathering the two returns; it is unacceptable for a moving camera.

Using the two camera approach (described in more detail in U.S. Pat. No. 4,862,257 to Ulich, dated Aug. 29, 1989 and incorporated herein by reference), a different set of problems is encountered. First, since the differential imaging must be achieved on a pixel-to-pixel basis, it is necessary to accurately align the focal planes between the cameras. Second, parallax due to the spatial separation between the two focal planes must be eliminated. Third, accurate timing synchronization between the two cameras is required. In principal, these factors can be successfully adjusted. However, when the assembly is allowed to move, vibratory and displacement effects ensure misalignment between the two cameras, making the differential image unsatisfactory.

While the conventional art systems are satisfactory under certain conditions, they are not entirely suitable in all environments, or applications (such as a moving camera). For example, carrying out mine sweeping operations in agitated or otherwise murky saltwater under harsh weather conditions would render accurate imaging of conventional systems highly problematical. Consequently, there is a need for accurate imaging under extreme environmental conditions for detecting objects in high dispersion or light scattering mediums such as saltwater.

SUMMARY OF THE INVENTION

Accordingly, it is one object of the present invention to improve visual optical detectability of a scene or object enveloped in a high dispersion or light-scattering medium.

It is another object of the present invention to provide an imaging system capable of operating under extreme light-scattering conditions of the medium, in particular, turbulence or a high level of particulate contamination, as well as applications regarding movement of the imaging system.

It is a further object of the present invention to provide an imaging system that is capable of relying upon only short bursts of illuminating light.

It is an additional object of the present invention to provide an imaging system having a greater stand off range than conventional imaging systems.

It is yet a further object of the present invention to provide an imaging system that is particularly effective for the detection of mines in seawater.

It is still a further object of the present invention to provide an imaging system that admits to modification for use in a wide variety of light scattering mediums, including water, fog and smoke.

These and other goals and objects of the present invention are achieved by a differential imaging system for object detection arranged to compare reflected signals from a single burst of illumination on a light scattering medium encompassing the object. This system includes a photosensitive area and a first device operatively connected to the photosensitive area for collecting a first portion of the reflected signal from the single burst of illumination. Also included is a second device operatively connected to the photosensitive area for collecting a second portion of the reflected signal from the single burst of illumination. A processing means is used for subtracting an adjusted value of the first portion from the second portion to provide signal data regarding the object.

Another aspect of the present invention is manifested by a method of generating a differential image of an object in a light scattering medium. The method includes the steps of illuminating a portion of the medium containing the object by a single burst of illuminating light thereby creating a reflected light signal. The first portion of the reflected light signal is collected on a photosensitive surface. This portion is transferred to a first storage device as a first stored image. Immediately following the first transfer, a second portion of the reflected light signal is collected on the same photosensitive surface, and then transferred to a second storage device as a second stored image. The first stored image is subtracted from the second stored image to obtain image data regarding the object.

DETAILED DESCRIPTION OF THE PREFERRED EMBODIMENTS

Figure 1:
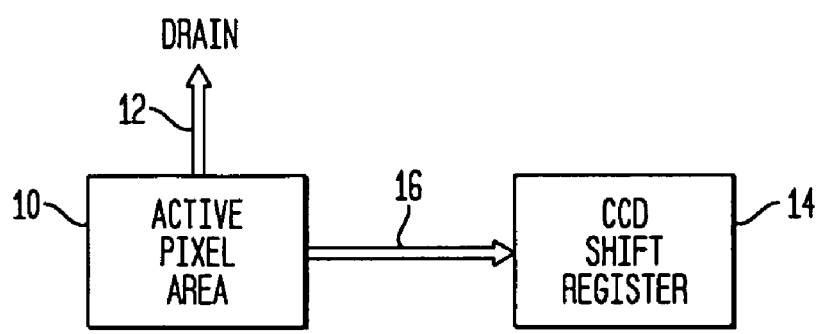
FIG. 1 is a schematic diagram depicting key elements in a conventional imaging system.

This invention builds on the focal plane advances of the conventional art, first by rearranging the focal plane (the arrangement of the photosensor array and storage registers), and second by incorporating additional circuitry (based upon that used in the conventional art) to accomplish the required control and signal handling functions. The present design has the capability of gating the photosensor array by controlling the output of photoelectrons generated in the active photosite in the same manner as shown schematically in the conventional art arrangement of FIG. 1, which is incorporated into the present invention.

The successful differential imaging provided by the present invention depends on the use of a common focal plane for successive returns of the reflected light from the single illumination burst. Also, it is necessary that the gating of successive reflective light signals that are used to create images be temporally very close together. This should take place on a time scale on the order of the duration of the single illumination burst.

Figure 2:
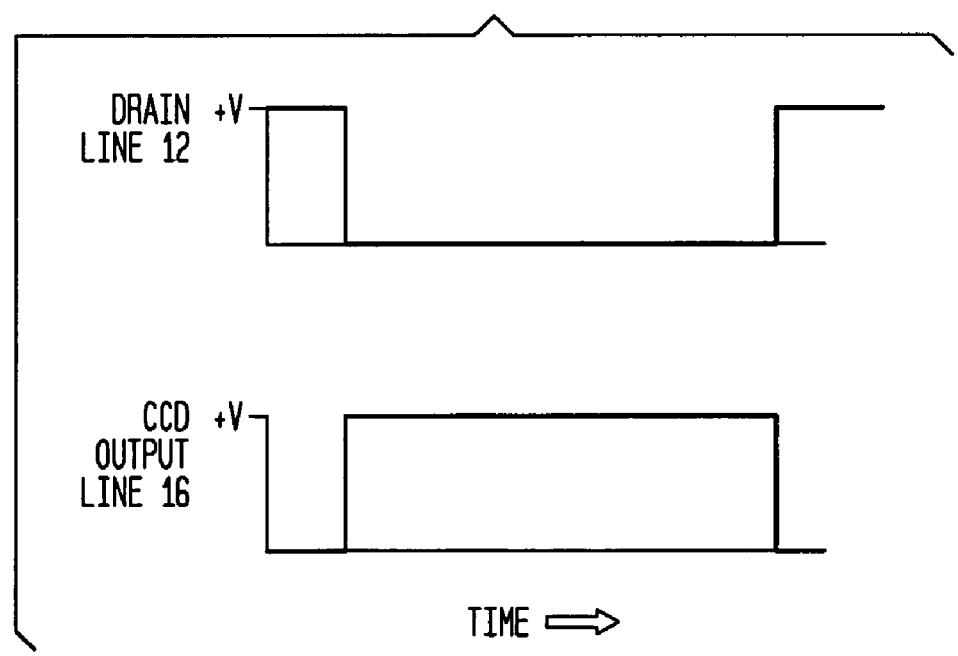
FIG. 2 is a timing diagram depicting the operation of a conventional imaging system.

The operating time diagram of a conventional device, incorporated into the present invention, is shown in FIG. 2. When the drain line 12 is at its operating positive voltage, it removes (drains) photoelectrons generated in the active pixel area 10. This is the quiescent state for the focal plane or photosensor array. When it is desired to gate the focal plane to collect light for an image, the drain voltage is dropped (to zero), and the output line 16 of the CCD shift register 14 is raised to the operating positive voltage. This allows the charge generated in the pixel area 10 to accumulate in the CCD shift register 14 (which acts to store the charge during the gate period). At the end of the gate duration, the voltages are returned to the quiescent state. The rise/fall of the applied voltage signal is on the order of 1 ns. Following the gate duration, all pixels in the focal plane will have accumulated charge in the CCD. These pixel signals (represented as charge packets in the corresponding CCD element) will be read out using standard CCD techniques.

If the desired image signal is represented as I, the scattering associated with the return signal S, and the scattering from the adjacent region as S', the following relationship exists for each pixel:

Return(2)=$I+S$

Return(1)=$S'$ $S=a*S'$, where a is a scaling constant relating the two scattering values. By adjusting a, one determines Differential Image=Return (2)−a*Return (1)=I producing the desired image.

The primary variable affecting the size of the scaling constant "a" (for spatially adjacent reflected signal returns along the light path) is the relative volume illuminated for both reflected signal returns. The signal return containing the image will not usually have the same spacial extent of the scattering volume as does that containing only a light scattering. A typical value for this scaling constant is on the order of 0.5-10, assuming that both range-gated regions have the same temporal gate duration.

Figure 3:
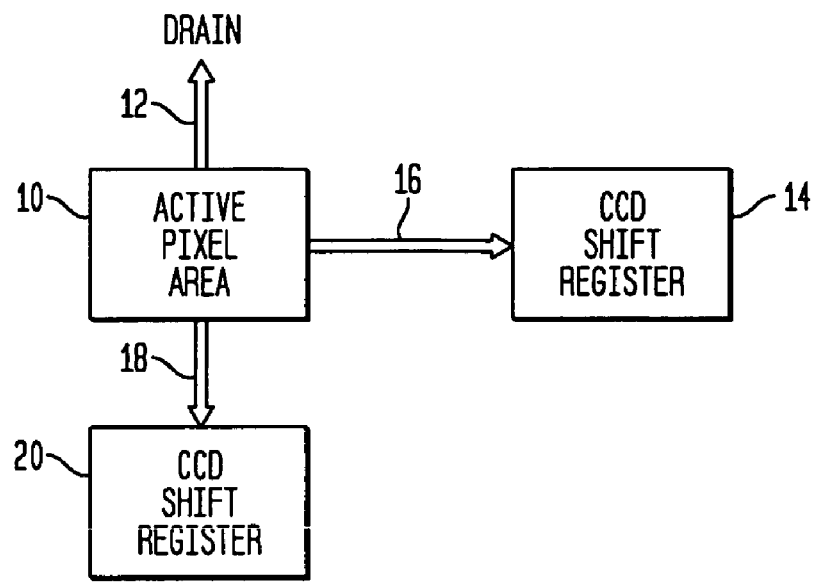
FIG. 3 is a schematic diagram depicting the physical arrangement of the present invention.

The changes to the focal plane involved in this invention are shown schematically in FIG. 3. They involve adding an additional CCD output line, an additional CCD output register 20, and changing the operating voltage-timing of the focal plane.

Figure 4:
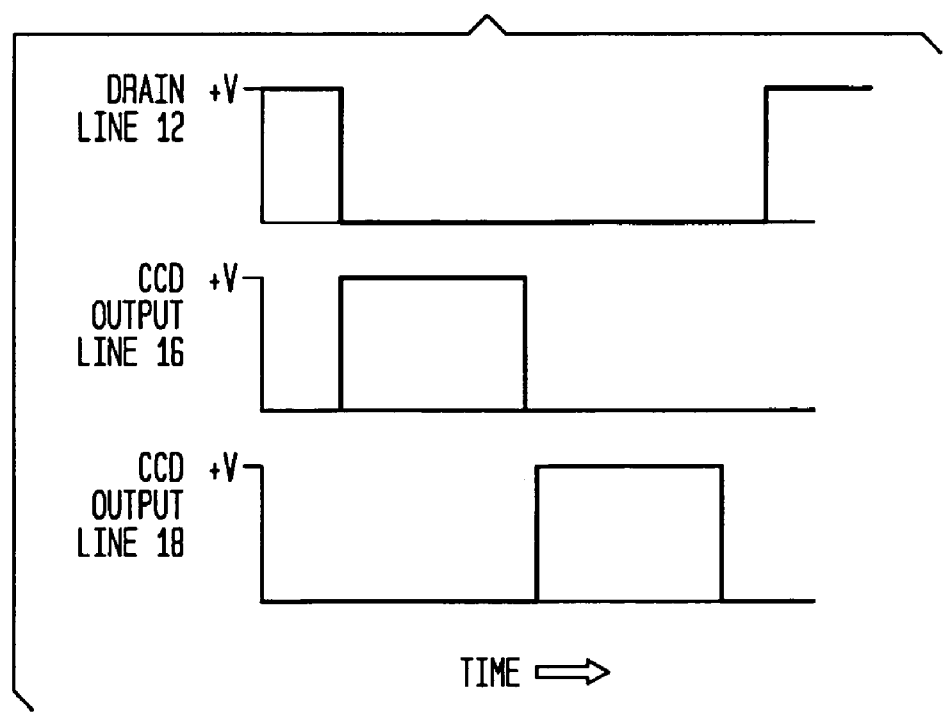
FIG. 4 is a timing diagram depicting the operation of the present invention.

FIG. 4 shows the voltage-timing diagram for the new configuration. As before, the drain line 12 is high while the focal plane or photosensor array 10 is quiescent (not accumulating signal). The drain line voltage is dropped in order for the focal plane to be active. First one output line (e.g., output line 16) and then the other (e.g., output line 18) are set to high potential (active), to accumulate the two reflected signals portions or returns from the single illumination burst. Each reflected signal portion or return is accumulated into its respective CCD output register 14,20. Since the identical pixel array or photosensitive area 10 is used for both signal portions, spatial registration between pixels automatically occurs. Representing the reflected signal portions present in each CCD register by the respective pixel values, the result is two reflected signal portions P(x,y,1) and P(x,y,2) representing two images of the illuminated scene.

A key aspect of this invention is the use of these signals once obtained. For the purpose of this example of the present invention, it is assumed that signal 1 occurs earlier than signal 2, even though for some embodiments it may be desirable for this order to be reversed. The first signal is scaled by a constant "a" (which may be pixel position dependent) as $S(x,y, 1)=a*P(x,y, 1)$ and then subtracted (on a pixel-by-pixel basis) from the second $I(x,y)=P(x,y, 2)-S(x,y, 1)$.

The output signal I(x,y) is the desired differential image. In order to accomplish this signal processing task, it is necessary to scale the first image (P (x,y1)) by a multiplication operation, and then to subtract the scaled image from the other image.

In setting the scaling constant (a), the operator will have control over this setting. The operator will set the value which achieves an optimum compromise between noise reduction and image quality in the differential image. Preferably, this value is in the range of 0.5-10. In some applications, it may prove advantageous for this value to be set automatically by a control algorithm, but this automatic setting is not an essential part of this invention.

In accomplishing the differential image, it is desirable to permit the operator to control the setting of the gate timing for the start of the first gate, the duration of each gate, and the start of the second gate. The reason for permitting the separate setting of each gate is to permit using either gate as the background subtraction field. The reasons for permitting the separate setting of each duration is to permit the operator to select regions of uniformity in the subtracted gate, and to optimize the return intensity from the image of interest. These controls, while a desirable feature of the invention, are an added feature, distinct from the basic invention.

As indicated above, the advantages of this invention are the formation of a differential image, using a single light pulse, in a manner ensuring registry of the individual pixels constituting this image. The advantages of this are:

(1) a higher-quality image;

(2) an image quality which is largely unaffected by external vibrations on the focal plane;

(3) a differential image gathered in such manner that the exact placement of scattering centers in the medium is essentially constant between the two differential image components. The net result of these advantages is to permit, for the first time, a practical system for performing differential imaging from a moving, vibrating platform.

The preferred alternative for implementation is to include all of the signal processing logic circuitry in charge mode. Doing so minimizes electronically-induced noise in charge mode. This also minimizes electronically-induced noise from the image. However, this implementation is not a necessary part of this invention.

Execution of the logic external to the focal plane substrate is a potential alternative. The use of an optical intensifier in connection with the differential imaging for providing better signals in low-light situations is an available alternative, when used with this arrangement. The use of scaling on each of the differential image, and the use of post-scaling of the differential image to better match external signal requirements are available alternatives. In conjunction with clip-on logic circuitry, the use of clip-on digitization of the differential image is a desirable alternative. There are also many possible alternatives for detailed circuitry layout and implementation to accomplish the desired differential imaging.

Although a number of embodiments have been disclosed by way of example, the present invention is not limited thereby. Rather, the present invention encompasses all variations, permutations, adaptations, modifications, as well any other version, form or embodiment that would occur to one skilled in this art, who has been taught the present invention by this application. Consequently, the present invention should be construed to be limited only by the following claims.

I claim:

1. A method of generating a differential image of an object in a light scattering medium, comprising the steps of:
   illuminating a portion of said light scattering medium with a single burst of illuminating light to generate reflected light therefrom;
   providing a charge generating photosensitive device in the path of said reflected light;
   activating said charge generating photsensitive device for a period of time during which a portion of said reflected light is collected by said charge generating photosensitive device in the form of a generated charge that is indicative of an image each instant of time during said period of time;
   providing a first charge storing device and a second charge storing device, each of which is independently operatively coupled to said charge generating photosensitive device;
   storing, on said first charge storing device, said generated charge present on said charge generating photosensitive device during a first part of said period of time wherein a first image is defined;
   storing, on said second charge storing device, said generated charge present on said charge generating photosensitive device during a remaining part of said period of time wherein a second image is defined; and
   generating a difference between (i) said generated charge associated with said first part of said period of time and (ii) said generated charge associated with said remaining part of said period of time.

2. A method according to claim 1 wherein said first part of said period of time and said remaining part of said period of time are the same in duration.

3. A method according to claim 1 wherein said first part of said period of time and said remaining part of said period of time are different in duration.

4. A method according to claim 1 further comprising the step of applying, prior to said step of generating, a scaling factor to one of (i) said generated charge associated with said first part of said period of time and (ii) said generated charge associated with said remaining part of said period of time.

5. A method according to claim 2 further comprising the step of applying, prior to said step of generating, a scaling factor to one of (i) said generated charge associated with said first part of said period of time and (ii) said generated charge associated with said remaining part of said period of time.

6. A method according to claim 5 wherein said scaling factor has a value in the range of approximately 0.5 to 10.

7. A method according to claim 1 further comprising the step of draining said generated charge from said charge generating photosensitive device when said period of time terminates.

8. A method of generating a differential image of an object in a light scattering medium, comprising the steps of:
   illuminating a portion of said light scattering medium with a single burst of illuminating light to generate reflected light therefrom;
   providing a charge generating photosensitive device in the path of said reflected light;
   activating said charge generating photsensitive device for a period of time during which a portion of said reflected light is collected by said charge generating photosensitive device in the form of a generated charge that is indicative of an image each instant of time during said period of time;
   providing a first charge coupling device (CCD) and a second charge coupling device (CCD), each of which is independently operatively coupled to said charge generating photosensitive device by means of a first output line and a second output line, respectively;
   simultaneously applying, during a first part of said period of time, a high potential to said first output line and a low potential to said second output line wherein said generated charge present on said charge generating photosensitive device during said first part of said period of time accumulates only on said first CCD and defines a first image;
   simultaneously applying, during a remaining part of said period of time, a high potential to said second output line and a low potential to said first output line wherein said generated charge present on said charge generating photosensitive device during said remaining part of said period of time accumulates only on said second CCD and defines a second image; and
   generating a difference between (i) said generated charge associated with said first part of said period of time and (ii) said generated charge associated with said remaining part of said period of time.

9. A method according to claim 8 wherein said first part of said period of time and said remaining part of said period of time are the same in duration.

10. A method according to claim 8 wherein said first part of said period of time and said remaining part of said period of time are different in duration.

11. A method according to claim 8 further comprising the step of applying, prior to said step of generating, a scaling factor to one of (i) said generated charge associated with said first part of said period of time and (ii) said generated charge associated with said remaining part of said period of time.

12. A method according to claim 9 further comprising the step of applying, prior to said step of generating, a scaling factor to one of (i) said generated charge associated with said first part of said period of time and (ii) said generated charge associated with said remaining part of said period of time.

13. A method according to claim 12 wherein said scaling factor has a value in the range of approximately 0.5 to 10.

14. A method according to claim 8 further comprising the steps of:
   draining said generated charge from said charge generating photosensitive device immediately prior to the commencement of said period of time; and
   draining said generated charge from said charge generating photosensitive device immediately after said period of time terminates.

15. A system for generating a differential image of an object in a light scattering medium when a portion of said light scattering medium has been illuminated with a single burst of illuminating light to generate reflected light therefrom, said system comprising:
   a charge generating photosensitive device placed in the path of said reflected light, wherein said charge generating photsensitive device is activated for a period of time during which a portion of said reflected light is collected by said charge generating photosensitive device in the form of a generated charge that is indicative of an image each instant of time during said period of time;
   a first charge coupling device (CCD) independently operatively coupled to said charge generating photosensitive device by a first output line;
   a second charge coupling device (CCD) independently operatively coupled to said charge generating photosensitive device by a second output line;
   means for simultaneously applying, during a first part of said period of time, a high potential to said first output line and a low potential to said second output line wherein said generated charge present on said charge generating photosensitive device during said first part of said period of time accumulates only on said first CCD and defines a first image;
   means for simultaneously applying, during a remaining part of said period of time, a high potential to said second output line and a low potential to said first output line wherein said generated charge present on said charge generating photosensitive device during said remaining part of said period of time accumulates only on said second CCD and defines a second image; and
   processing means for generating a difference between (i) said generated charge associated with said first part of said period of time and (ii) said generated charge associated with said remaining part of said period of time.

16. A system as in claim 15 further comprising means, coupled to said charge generating photosensitive device, for draining said generated charge from said charge generating photosensitive device immediately prior to the commencement of said period of time, and for draining said generated charge from said charge generating photosensitive device immediately after said period of time terminates.

17. A system as in claim 16 wherein said means for draining comprises a drain line having a high potential applied thereto while each of said first output line and said second output line have a low potential applied thereto.

* * * * *